(12) United States Patent
Ranchod et al.

(10) Patent No.: US 10,966,603 B2
(45) Date of Patent: Apr. 6, 2021

(54) MULTIPLE OFF-AXIS CHANNEL OPTICAL IMAGING DEVICE WITH OVERLAP TO REMOVE AN ARTIFACT FROM A PRIMARY FIXATION TARGET

(71) Applicant: BROADSPOT IMAGING CORP, Emeryville, CA (US)

(72) Inventors: Tushar M. Ranchod, Berkeley, CA (US); Benjamin A. Jacobson, Santa Barbara, CA (US); Clark Pentico, Simi Valley, CA (US)

(73) Assignee: BROADSPOT IMAGING CORP, Emeryville, CA (US)

( * ) Notice: Subject to any disclaimer, the term of this patent is extended or adjusted under 35 U.S.C. 154(b) by 228 days.

(21) Appl. No.: 16/226,357

(22) Filed: Dec. 19, 2018

(65) Prior Publication Data

US 2019/0200855 A1    Jul. 4, 2019

Related U.S. Application Data

(60) Provisional application No. 62/611,076, filed on Dec. 28, 2017.

(51) Int. Cl.
| | |
|---|---|
| *A61B 3/00* | (2006.01) |
| *A61B 3/15* | (2006.01) |
| *A61B 3/13* | (2006.01) |
| *A61B 3/117* | (2006.01) |
| *A61B 3/12* | (2006.01) |

(52) U.S. Cl.
CPC .......... *A61B 3/0058* (2013.01); *A61B 3/0091* (2013.01); *A61B 3/117* (2013.01); *A61B 3/12* (2013.01); *A61B 3/132* (2013.01); *A61B 3/152* (2013.01); *A61B 3/158* (2013.01)

(58) Field of Classification Search
CPC ..... A61B 3/0091; A61B 3/0058; A61B 3/132; A61B 3/158
USPC ................................ 351/219, 246, 211, 221
See application file for complete search history.

(56) References Cited

U.S. PATENT DOCUMENTS

| | | | |
|---|---|---|---|
| 5,024,518 A * | 6/1991 | Richards | ................ A61B 3/125 351/219 |
| 5,976,096 A | 11/1999 | Shimizu et al. | |
| 7,140,730 B2 | 11/2006 | Wei et al. | |
| 7,854,510 B2 | 12/2010 | Verdooner et al. | |

(Continued)

OTHER PUBLICATIONS

International Search Report dated Apr. 1, 2019 as received in Application No. PCT/US2018/067401.

(Continued)

*Primary Examiner* — Zachary W Wilkes
(74) *Attorney, Agent, or Firm* — Maschoff Brennan

(57) ABSTRACT

An optical imaging device includes a support structure and imaging channels, where each imaging channel includes a discrete optical imaging pathway. The imaging channels may be disposed within the support structure, and the imaging channels may be aimed at different angles relative to each other such that each optical imaging pathway is directed towards a pupil of the eye. Additionally, the optical imaging device may include a primary fixation target configured to emit optical signals along a primary fixation target projection path towards the pupil of the eye. Further, an artifact of the primary fixation target may be generated onto a portion of the eye to be imaged.

12 Claims, 9 Drawing Sheets

(56) References Cited

U.S. PATENT DOCUMENTS

| | | | |
|---|---|---|---|
| 8,550,626 B2* | 10/2013 | Griggio | A61B 3/0091 |
| | | | 351/206 |
| 8,714,743 B2 | 5/2014 | Verdooner | |
| 8,807,751 B2 | 8/2014 | Kahn et al. | |
| 9,295,388 B2 | 3/2016 | Lawson et al. | |
| 9,314,155 B2 | 4/2016 | Verdooner | |
| 9,480,394 B2 | 11/2016 | Verdooner | |
| 9,521,950 B2 | 12/2016 | Verdooner | |
| 2008/0077854 A1 | 3/2008 | Alabi | |
| 2009/0153796 A1 | 6/2009 | Rabner | |
| 2010/0195048 A1 | 8/2010 | Hammer et al. | |
| 2011/0234978 A1 | 9/2011 | Hammer et al. | |
| 2012/0249957 A1 | 10/2012 | Shibata et al. | |
| 2012/0287255 A1 | 11/2012 | Ignatovich et al. | |
| 2013/0107277 A1 | 5/2013 | Hirose et al. | |
| 2013/0250243 A1 | 9/2013 | Cech | |
| 2013/0271728 A1 | 10/2013 | Ranchod | |
| 2015/0320308 A1 | 11/2015 | Akiba et al. | |
| 2016/0135679 A1 | 5/2016 | Frisken et al. | |
| 2017/0314908 A1 | 11/2017 | Chong | |

OTHER PUBLICATIONS

Written Opinion of the International Searching Authority dated Apr. 1, 2019 as received in Application No. PCT/US2018/067401.
Götzinger et al. "Polarization maintaining fiber based ultra-high resolution spectral domain polarization sensitive optical coherence tomography" Opt. Express, vol. 17(25), pp. 22704-22717; Dec. 7, 2009.

* cited by examiner

MULTIPLE OFF-AXIS CHANNEL OPTICAL IMAGING DEVICE WITH OVERLAP TO REMOVE AN ARTIFACT FROM A PRIMARY FIXATION TARGET

FIELD

The application relates generally to a multiple off-axis channel optical imaging device with overlap to remove an artifact from a primary fixation target.

BACKGROUND

Ocular imaging is commonly used both to screen for diseases and to document findings discovered during clinical examination of the eye. Specifically, documentation and analysis of optical imaging may be relevant to comprehensive eye examinations and full evaluations of current conditions, treatment, and/or early prevention of various eye conditions and diseases. Artifacts from fixation targets may affect optical imaging.

The subject matter claimed herein is not limited to embodiments that solve any disadvantages or that operate only in environments such as those described above. Rather, this background is only provided to illustrate one example technology area where some embodiments described herein may be practiced.

SUMMARY

An optical imaging device may include a support structure and a plurality of imaging channels, where each imaging channel of the plurality of imaging channels may include a discrete optical imaging pathway. Additionally, the plurality of imaging channels may be disposed within the support structure, and the plurality of imaging channels may be aimed at different angles relative to each other such that each optical imaging pathway is directed towards a pupil of the eye. The optical imaging device may further include a primary fixation target configured to emit optical signals along a primary fixation target projection path towards the pupil of the eye. In some embodiments, an artifact of the primary fixation target may be generated onto a portion of the eye to be imaged.

The objects and advantages of the embodiments will be realized and achieved at least by the elements, features, and combinations particularly pointed out in the claims.

Both the foregoing general description and the following detailed description are given as examples and are explanatory and are not restrictive of the invention, as claimed.

BRIEF DESCRIPTION OF THE DRAWINGS

Example embodiments will be described and explained with additional specificity and detail through the use of the accompanying drawings in which.

DESCRIPTION OF EMBODIMENTS

In some embodiments of the present disclosure, imaging channels, each with at least one unique imaging pathway, may approach the eye at different angles. The respective imaging pathways may cross each other within the plane of the iris of the human eye, or within the space between the cornea and the mid-vitreous cavity, or at any point between the retina and the cornea. In these or other embodiments, none of the imaging channels may be coaxial with a central axis of the eye. However, in some embodiments, at least one imaging channel may be coaxial with the central axis of the eye.

The imaging channels may image different but partially overlapping regions of the eye such that the resulting images may be stitched into a single composite optical image with a combined area greater than any constituent image and in such a way that gaps may not appear within the composite image. For example, a first image may correspond to a first optical region; a second image may correspond to a second optical region; and a third image may correspond to a third optical region. In this example, each region may be overlapped by at least one other region. Continuing with the example, the three example images may be gathered, and the overlap regions may be averaged or homogenized for clarity and continuity thereby helping to create a single contiguous image of all three regions based on the three individual images. In these or other embodiments, images (whether individual images or composite images) may be stored in a storage device coupled to the optical imaging device. In these or other embodiments, more or fewer than three images may comprise a composite image.

In some embodiments, a primary fixation target may be used for a patient to focus on to properly align the eye with the imaging device. However, the use of such a primary fixation target may create artifacts in images being acquired of the eye, for example, when a projection path of the primary fixation target utilizes some or all of the same lenses as one of the optical imaging pathways. The artifact may include, for example: a shadow of the primary fixation target cast onto a portion of the eye to be imaged; a blurred, blackened, or obscured portion that corresponds to the primary fixation target, e.g., as depicted in an unfocused foreground of an image that is focused on a portion of the eye; and/or a display of optical signals emitted from the primary fixation target that intersect the portion of the eye to be imaged. Embodiments of an optical imaging device of the present disclosure may be configured to generate composite images enabling removal of such artifacts.

Figure 1A:
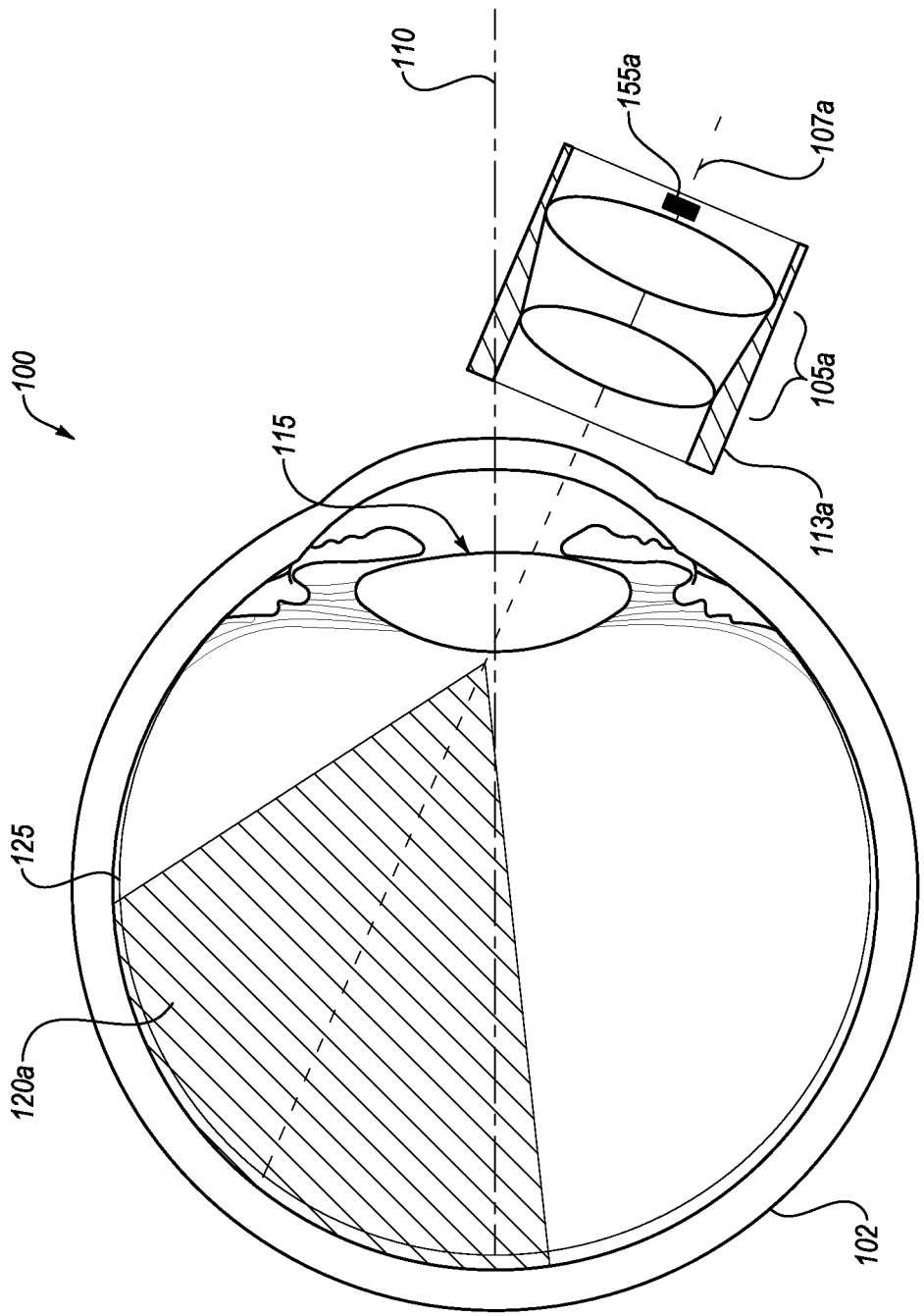
FIG. 1A illustrates a cross-sectional side view of an eye, including an example optical imaging pathway for imaging the eye.
Figure 1B:
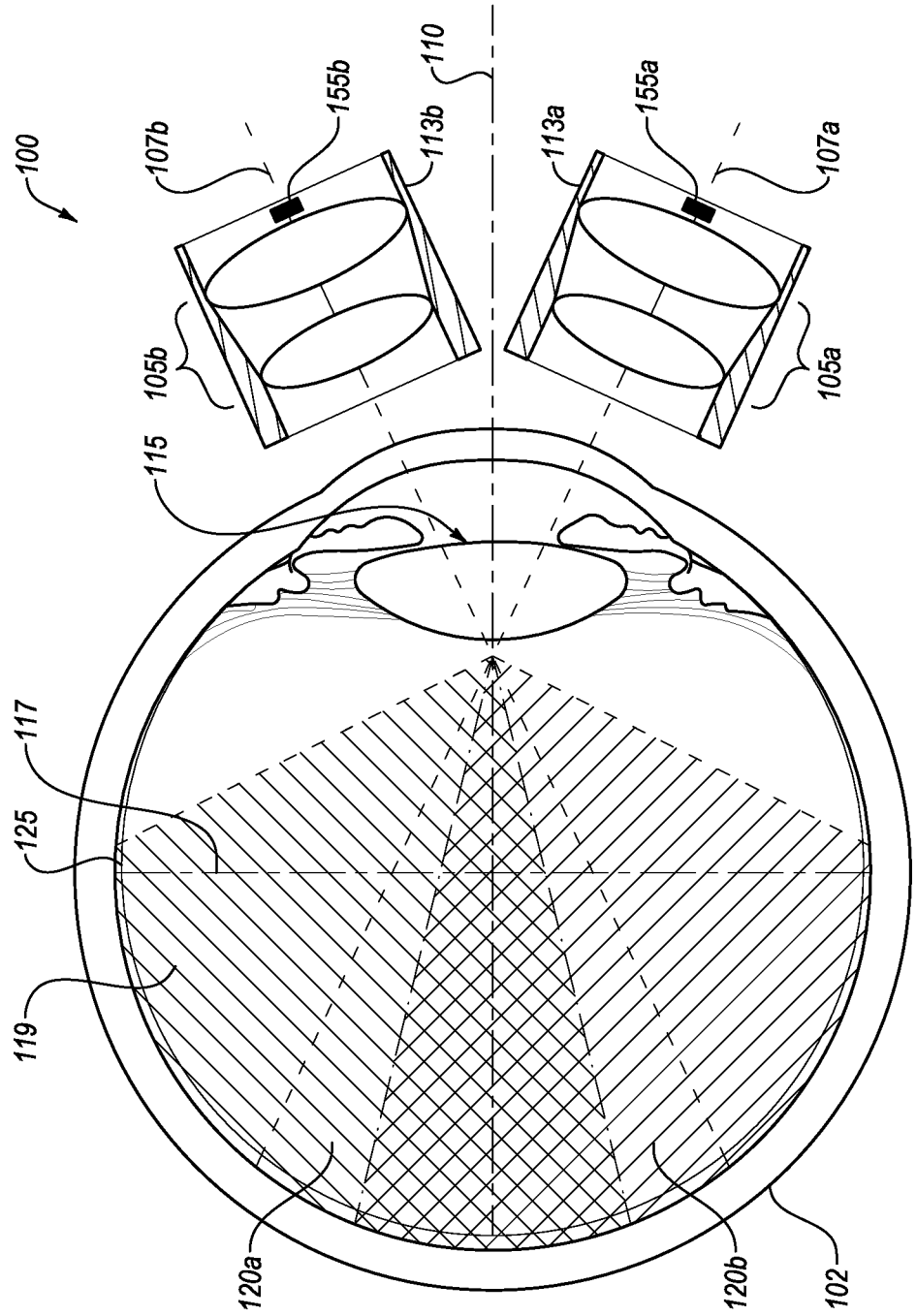
FIG. 1B illustrates another cross-sectional side view of the eye of FIG. 1A, including multiple example optical imaging pathways for imaging the eye.
Figure 1C:
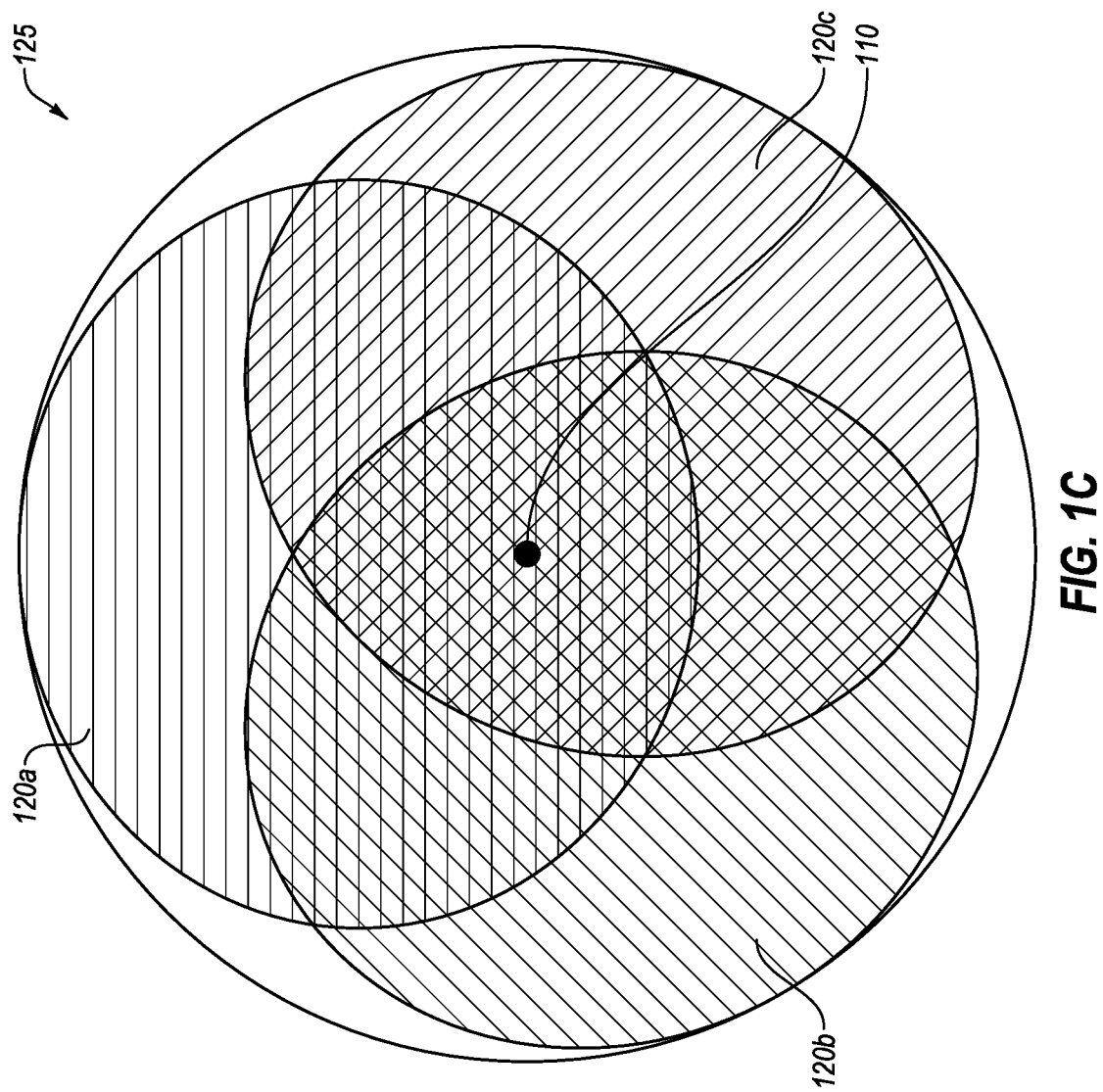
FIG. 1C illustrates a cross-sectional front view of the eye of FIG. 1A, including multiple overlapping imaging regions of the eye.

FIGS. 1A-1C indicate an example progression for achieving a composite optical image. For example, FIG. 1A illustrates a cross-sectional side view of an eye 102, including an example optical imaging pathway 107a for imaging the eye 102. FIG. 1B illustrates the same cross-sectional side view of the eye 102 with the addition of a second example optical imaging pathway 107b for imaging the eye 102. FIG. 1C illustrates three overlapping imaging regions 120a, 120b, and 120c for imaging an example area of the eye 102, including a retina 125. FIG. 1A also illustrates an imaging channel 113a, an eye lens 115, optical lenses 105a, a central axis 110, an imaging region 120a, and an image capturing device 155a. In these or other embodiments, the optical imaging pathway 107a may proceed from within the imaging channel 113a of a device (such as the device 200/300 illustrated in FIGS. 2A/2B and FIG. 3), through the pupil and the eye lens 115, and to the retina 125. Additionally or alternatively, the optical imaging pathway 107a may start and/or end at the image capturing device 155a, and the image capturing device 155a may be positioned anywhere within the imaging channel 113a. For example, the imaging capturing device 155a may be positioned between the optical lenses 105a, along a central axis of the imaging channel 113a normal to the eye 102, and/or off the central axis of the imaging channel 113a normal to the eye 102. In these or other embodiments, the optical imaging pathway 107a may be a center axis of a field of view of the image capturing device 155a.

Additionally or alternatively, the imaging region 120a may correspond to the optical imaging pathway 107a. For example, an area of the retina 125 that is covered by or is adjacent to the optical imaging pathway 107a may define the metes and bounds of the imaging region 120a. In other embodiments, other areas of the eye 102, such as the cornea, the iris, the iridocorneal angle, the sclera, and any other suitable area of the eye 102, whether in the anterior or posterior chamber of the eye 102, may be imaged.

In some embodiments, the optical lenses 105a may be housed by the imaging channel 113a and may collimate illumination light proceeding through the imaging channel 113a such that the illumination light proceeds collinear with and/or parallel to the optical imaging pathway 107a and illuminates at least a portion of the imaging region 120a. In some embodiments, the optical lenses 105a may be sized and shaped to fill an inner diameter of the imaging channel 113a that houses the optical lenses 105a, while in other embodiments, the optical lenses 105a may be sized and shaped to be less than the inner diameter of the imaging channel 113a. Additionally or alternatively, the optical lenses 105a may focus, disperse, and/or otherwise alter light transmission to enhance imaging capability of the image capturing device 155a to image the imaging region 120a. In these or other embodiments, the image capturing device 155a may be an imaging device or sensor that may respectively include an entire imaging sensor or a portion of a larger digital camera, where the larger digital camera may be positioned outside of the optical imaging device.

In some embodiments, other optical elements may also be included within the imaging channel 113a. For example, a prism may be positioned anywhere within the imaging channel 113a, e.g., between the optical lenses 105a, at a distal end of the imaging channel 113a and/or at a proximal end of the imaging channel positioned between the eye 102 and the optical lenses 105a. In some embodiments, the prism may be configured as a mirror, beam splitter, or other suitable reflective element (e.g., partially reflective, substantially reflective, or completely reflective). In these or other embodiments, multiple prisms may be positioned within the imaging channel 113a, while in other embodiments, only a single prism may be positioned within the imaging channel 113a. In some embodiments, the prism may help direct light to and/or from the eye 102, e.g., permitting multi-directional travel of optical signals between the eye 102 and an optical imaging device. For example, the prism may at least partially direct one or both of the optical imaging pathway 107a and an optical illumination pathway toward the eye 102.

In some embodiments, the optical imaging pathway 107a may not be coaxial to the central axis 110 of the eye 102. In this manner, multiple optical imaging pathways 107 (such as the optical imaging pathways 107a and 107b as shown in FIG. 1B) may enable imaging of the retina 125 and/or other areas of the eye 102, such as the cornea, the iris, the iridocorneal angle, the sclera, and any other suitable area of the eye 102, whether in the anterior or posterior chamber of the eye 102.

Additionally or alternatively, the optical lenses 105a may have fixed or variable positions within the imaging channel 113a. For example, one or more of the optical lenses 105a may be positionally fixed such that the optical lenses 105a may not move within the imaging channel 113a. As another example, one or more of the optical lenses 105a may be positionally movable within the imaging channel 113a such that the lenses may slide closer to the eye 102 during examination or slide farther away from the eye 102 during examination. Additionally or alternatively, the optical lenses 105a may be positionally movable within the imaging channel 113a such that the lenses may slide laterally so as to maintain a relative distance between the optical lenses 105a and the eye 102 during examination or image acquisition. Additionally or alternatively, the optical lenses 105a may be fixed positionally, but movable at the fixed position. For example, at least one of the optical lenses 105a may be angularly varied in orientation within the imaging channel 113a such that an angular orientation of the at least one optical lens 105a may be changed to or positioned at any angle such as perpendicular to the optical imaging pathway 107a, parallel to the optical imaging pathway 107a, and any suitable angle therebetween. In this manner, different imaging regions may be obtained and/or optical properties adjusted for lighting and/or imaging.

FIG. 1B illustrates another cross-sectional side view of the eye 102 of FIG. 1A, including multiple example optical imaging pathways 107 (such as the optical imaging pathways 107a and 107b) for imaging the retina 125 and/or other areas of the eye 102, such as the cornea, the iris, the iridocorneal angle, the sclera, and any other suitable area of the eye 102, whether in the anterior chamber or a posterior cavity 119 of the eye 102. Specifically, FIG. 1B shows the addition of an imaging channel 113b, an optical imaging pathway 107b, optical lenses 105b, overlapping imaging regions 120a/120b, and an image capturing device 155b.

The imaging channel 113b, the optical imaging pathway 107b, the optical lenses 105b, and the image capturing device 155b may be the same as or similar to the imaging channel 113a, the optical imaging pathway 107a, the optical lenses 105a, and the image capturing device 155a, respectively, of FIG. 1A. In some embodiments, more or fewer image capturing devices 155 may be utilized in the optical imaging device, e.g., depending on an imaging application or pupil size of the eye to be imaged.

Additionally or alternatively, the imaging channel 113b and/or the optical imaging pathway 107b may not be coaxial to the central axis 110 of the eye 102. Thus, in some embodiments, the optical imaging pathways 107 of the imaging channels 113 may be angled relative to each other and/or to the central axis 110. For example, in some embodiments, the optical imaging pathways 107 may cross each other at a position within the posterior cavity 119 of the eye 102, and at a position anterior to an equatorial line 117, e.g., when imaging the retina 125. In other embodiments, depending on the desired target area of the eye 102 to be imaged, such as a surface of the cornea, the iris, the iridocorneal angle or the sclera, the optical imaging pathways 107 may converge at a position in the anterior chamber or at a position anterior to an outer surface of the cornea. In other embodiments, depending on the desired target area of the eye 102 to be imaged, the optical imaging pathways 107 may converge at a position in the posterior cavity 119 of the eye 102, and at a position posterior to an equatorial line 117.

In these or other embodiments, the imaging region 120a may correspond to the optical imaging pathway 107a, and the imaging region 120b may correspond to the optical imaging pathway 107b. The imaging regions 120a/120b may include portions of, for example, the retina 125 that are captured in digital images. Additionally or alternatively, the imaging region 120a and the imaging region 120b may overlap, for example, such that one or more portions of the retina 125 are captured in both images through the imaging channels 113a and 113b.

In some embodiments, imaging channels 113 may be fixed relative to each other, exactly or approximately, in terms of position in three-dimensional space or in terms of angles relative to a central optical axis of each imaging channel or the central axis 110 of the eye 102. For example, the imaging channels 113 may be angled at approximately equal angles off of the central optical axis of each imaging channel 113. Additionally or alternatively, the imaging channels 113 may be angled at approximately equal angles off of the central axis 110 of the eye 102 of the patient such that the imaging channels 113 may be evenly spaced in the three hundred and sixty degrees around the central axis 110 of the eye 102 (e.g., each imaging channel 113 offset by approximately 30 degrees to approximately 45 degrees from the central axis 110 of the eye 102 and/or distributed approximately 120 degrees relative to each other).

In some embodiments, the angles between the imaging channels 113 relative to the central optical axis of each imaging channel 113 or relative to the central axis 110 of the eye 102 may not be equal or consistent. For example, different angles may accommodate different configurations and shapes of facial structures (e.g., a triangular base other than an equilateral triangle may be incorporated). In these or other embodiments, various configurations and numbers of imaging channels 113 may be used. For example, in some embodiments, four or five imaging channels 113 may be used in the optical imaging device 300 (not shown), while in other embodiments, between six and ten imaging channels 113 may be used, while in still other embodiments, only two imaging channels 113 may be used.

In some embodiments, the known relative positioning of the multiple imaging channels 113 may facilitate the stitching of multiple images into a composite image via software analytics. Thus, according to some embodiments, regardless of the angles (equal or not) of the imaging channels 113 relative to the central axis 110 of the eye 102 or relative to the central optical axis of each imaging channel, the angles may be known variables to the software such that image stitching may be achieved with sufficient precision. The multiple images to be stitched into a composite image, which are obtained via the image capturing devices 155 within the imaging channels 113, may be stored in a storage device.

FIG. 1C illustrates a cross-sectional front view of the eye 102 of FIG. 1A, including multiple overlapping imaging regions 120a/120b/120c of the retina 125. In other embodiments, the multiple overlapping imaging regions 120a/120b/120c may correspond to other areas of the eye 102, such as the cornea, the iris, the iridocorneal angle, the sclera, and any other suitable area of the eye 102, whether in the anterior chamber or a posterior cavity 119 of the eye 102. With the three different but overlapping imaging regions 120a/120b/120c of, for example, the retina 125, a composite image may be obtained that includes a combined area with a greater field of view than any single imaging region 120 and with fewer or no gaps within the composite image area. In some embodiments, the central axis 110 of the eye 102 may intersect a position on the retina 125 that is within two or more of the imaging regions 120.

In these or other embodiments of the present disclosure, an optical imaging device (such as that shown in FIG. 3) may include an upside-down pyramidal configuration of imaging channels 113 for increasing a clearance distance relative to facial structures of patients. In other embodiments, additional configurations of the imaging channels 113, other than for an upside-down pyramidal configuration of the optical imaging device, may be implemented. For example, any suitable configuration permitting additional or increased clearance between the optical imaging device and one or both of a brow and a nose is contemplated herein. Additionally or alternatively, any suitable configuration permitting multiple imaging channels 113, e.g., two or more imaging channels 113, for imaging the eye 102 may be implemented.

Modifications, additions, or omissions may be made to the embodiments of FIGS. 1A-1C without departing from the scope of the present disclosure. For example, in some embodiments, the channels 113a/113b may include any number of other components that may not be explicitly illustrated or described. Additionally or alternatively, for example, the imaging regions 120a/120b/120c may include different sizes, shapes, overlapping areas, etc. than may be explicitly illustrated or described.

Figure 2A:
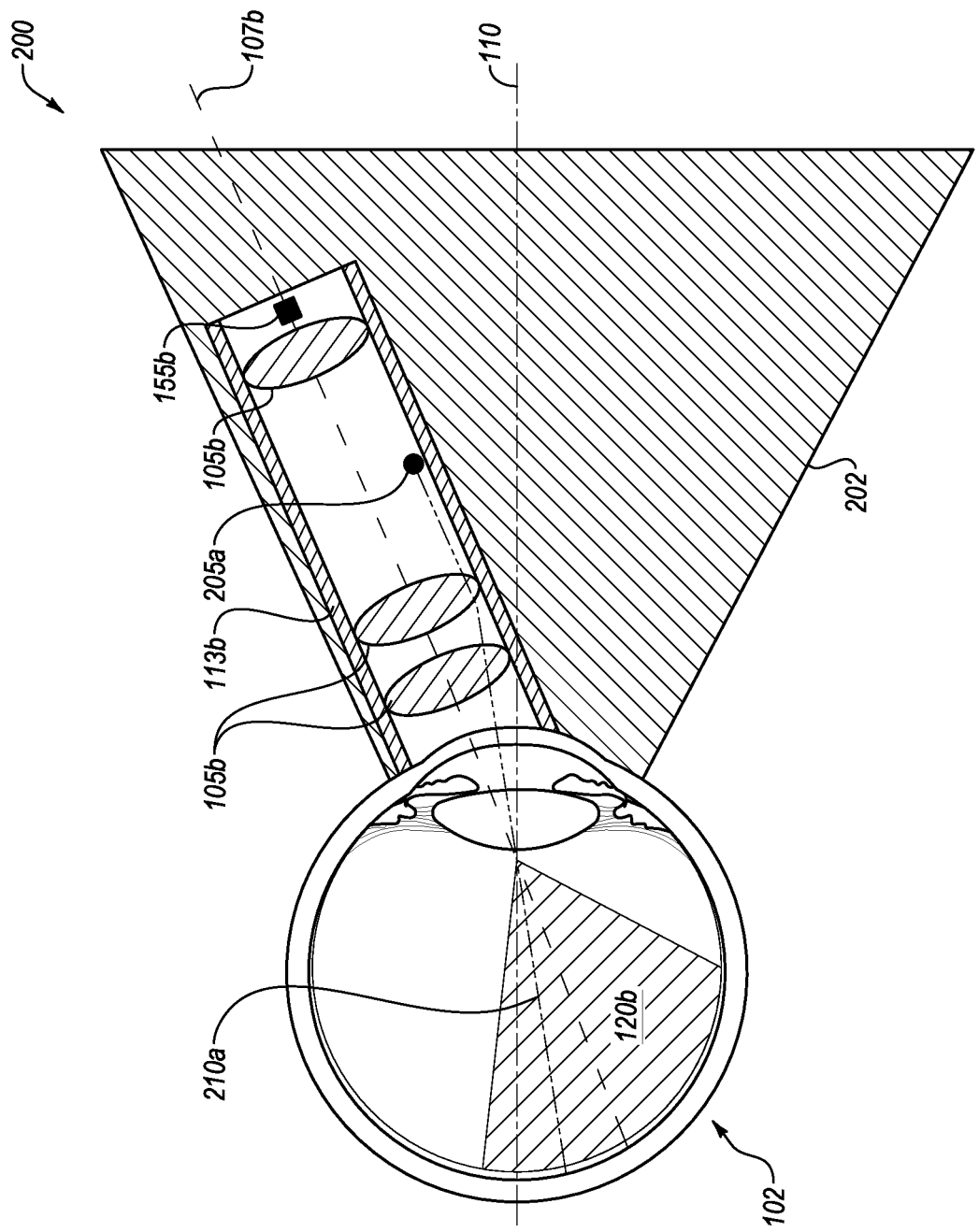
FIG. 2A illustrates an example embodiment of a cross-sectional side view of an optical imaging device using primary fixation for imaging the eye.

FIG. 2A illustrates an example embodiment of a cross-sectional side view of an optical imaging device 200 using primary fixation for imaging the eye 102, all arranged according to one or more embodiments of the present disclosure. As illustrated, the optical imaging device 200 includes the optical lenses 105b, the optical imaging pathway 107b, the imaging channel 113b, and the image capturing device 155b of FIGS. 1A-1B. Additionally, FIG. 2A illustrates a support structure 202, a primary fixation target 205a, and a primary fixation target projection path 210a.

The support structure 202 may house the optical lenses 105b, the imaging channels 113b, and the image capturing devices 155b. Additionally or alternatively, the support structure 202 may be sized and shaped for ergonomic purposes, e.g., to more suitably interface with facial features of a patient. In other embodiments, additional configurations of the support structure 202, other than a triangular shape or pyramidal configuration, may be implemented. For example, any suitable configuration permitting additional or increased clearance between the support structure 202 and one or both of a brow and a nose is contemplated herein. Additionally or alternatively, any suitable configuration permitting multiple imaging channels 113, e.g., two or more imaging channels 113, for imaging the eye 102 may be implemented.

In some embodiments, one or more of the optical lenses 105b may be a common lens that shares both the optical imaging pathway 107b and the primary fixation target projection path 210a. However, in other embodiments, the primary fixation target 205a may be positioned within the imaging channel 113b in such a manner so as to not share any of the optical lenses 105b with the optical imaging pathway 107b. In these and other embodiments, the primary fixation target 205a may or may not generate an artifact on images obtained of the imaging region 120b.

In some embodiments, the primary fixation target projection path 210a may correspond to the primary fixation target 205a. For example, the primary fixation target projection path 210a may include an optical axis or an optical direction that optical signals produced by the primary fixation target 205a may be generally directed along. Additionally or alternatively, the primary fixation target projection path 210a may include an optical pathway that optical signals produced by the primary fixation target 205a may generally follow. Obstruction of optical signals may alter an actual path of the optical signals produced by the primary fixation target 205a, and thus, in some embodiments, the primary fixation target projection path 210a may not necessarily include an actual path of the optical signals, for example, all the optical signals, produced by the primary fixation target 205a. Some optical signals produced by the primary fixation target 205a may be blocked or obstructed along the primary fixation target projection path 210a, e.g., by an iris. In these or other embodiments, the primary fixation target projection path 210a may proceed from the primary fixation target 205a, through one or more optical elements such as the optical lenses 105b, to the eye 102, e.g., onto a fovea 230 illustrated in FIG. 2C of the eye 102. In some embodiments, the primary fixation target 205a may be positioned anywhere within the imaging channel 113b. Additionally or alternatively, the primary fixation target 205a may be positioned outside of the imaging channel 113b, e.g., as shown for a primary fixation target 205b in FIG. 2B.

In some embodiments, utilization of primary fixation and the primary fixation target 205a may result in a center axis of the support structure 202 being collinear with the central axis 110 of the eye 102. In this manner, the primary fixation target 205a may help to align the optical imaging device 200 with the central axis 110 of the eye 102. In these or other embodiments, the primary fixation target 205a may be a visual aid that the eye 102 of the patient can fixate upon. When the eye 102 fixates on the primary fixation target 205a, image acquisition of the eye may be performed by the image capturing device 155b. However as described in greater detail below, for example in conjunction with FIG. 2C, the primary fixation target 205a may result in an artifact of the primary fixation target 205a being imaged.

Figure 2B:
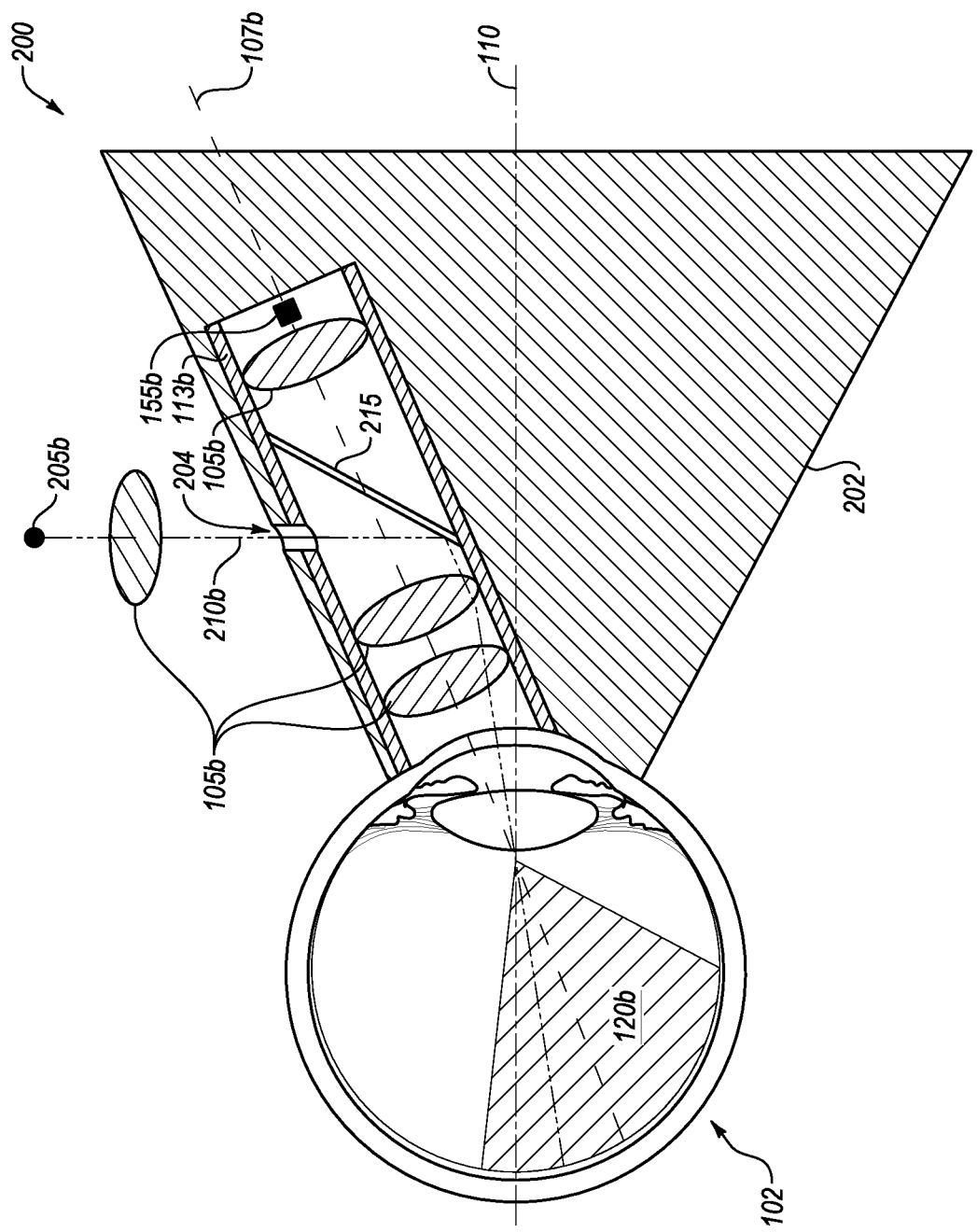
FIG. 2B illustrates another example embodiment of a cross-sectional side view of the optical imaging device of FIG. 2A using primary fixation for imaging the eye.

FIG. 2B illustrates another example embodiment of a cross-sectional side view of the optical imaging device 200 using primary fixation for imaging the eye 102, all arranged according to one or more embodiments of the present disclosure. As illustrated, the optical imaging device 200 includes the optical lenses 105b, the optical imaging pathway 107b, the imaging channel 113b, and the image capturing device 155b of FIGS. 1A-1B. Additionally, FIG. 2B illustrates the support structure 202 of FIG. 2A along with an optical byway 204, a primary fixation target 205b, a primary fixation target projection path 210b, and a prism 215.

In some embodiments, the primary fixation target 205b and the primary fixation target projection path 210b may be the same as or similar to the primary fixation target 205a and the primary fixation target projection path 210a, respectively, of FIG. 2A. For example, the primary fixation target 205b may be positioned differently than the primary fixation target 205a of FIG. 2A, e.g., outside of the imaging channel 113b. In this manner, the primary fixation target projection path 210b may proceed from the primary fixation target 205b, through one or more optical elements such as one of the optical lenses 105b, through the optical byway 204 to impinge the prism 215, through one or more additional optical elements such as the optical lenses 105b, and to the eye 102, e.g., onto the fovea 230 illustrated in FIG. 2C of the eye 102.

In some embodiments, the prism 215 may be configured as a mirror, beam splitter, or other suitable reflective element (e.g., partially reflective, substantially reflective, or completely reflective). In these or other embodiments, multiple prisms 215 may be positioned within the imaging channel 113b, while in other embodiments, only a single prism 215 may be positioned within the imaging channel 113a. Additionally or alternatively, the prism 215 may help direct light to and/or from the eye 102, e.g., permitting multi-directional travel of optical signals between the eye 102 and the optical imaging device 200.

In some embodiments, the optical byway 204 may be a thru-hole between inside the imaging channel 113b and outside the support structure 202. Additionally or alternatively, the optical byway 204 may be configured as an optically transparent section of the support structure 202 and wall of the imaging channel 113b such that at least a portion of optical signals transmitted from the primary fixation target 205b passes through the optical byway 204 into the imaging channel 113b.

Figure 2C:
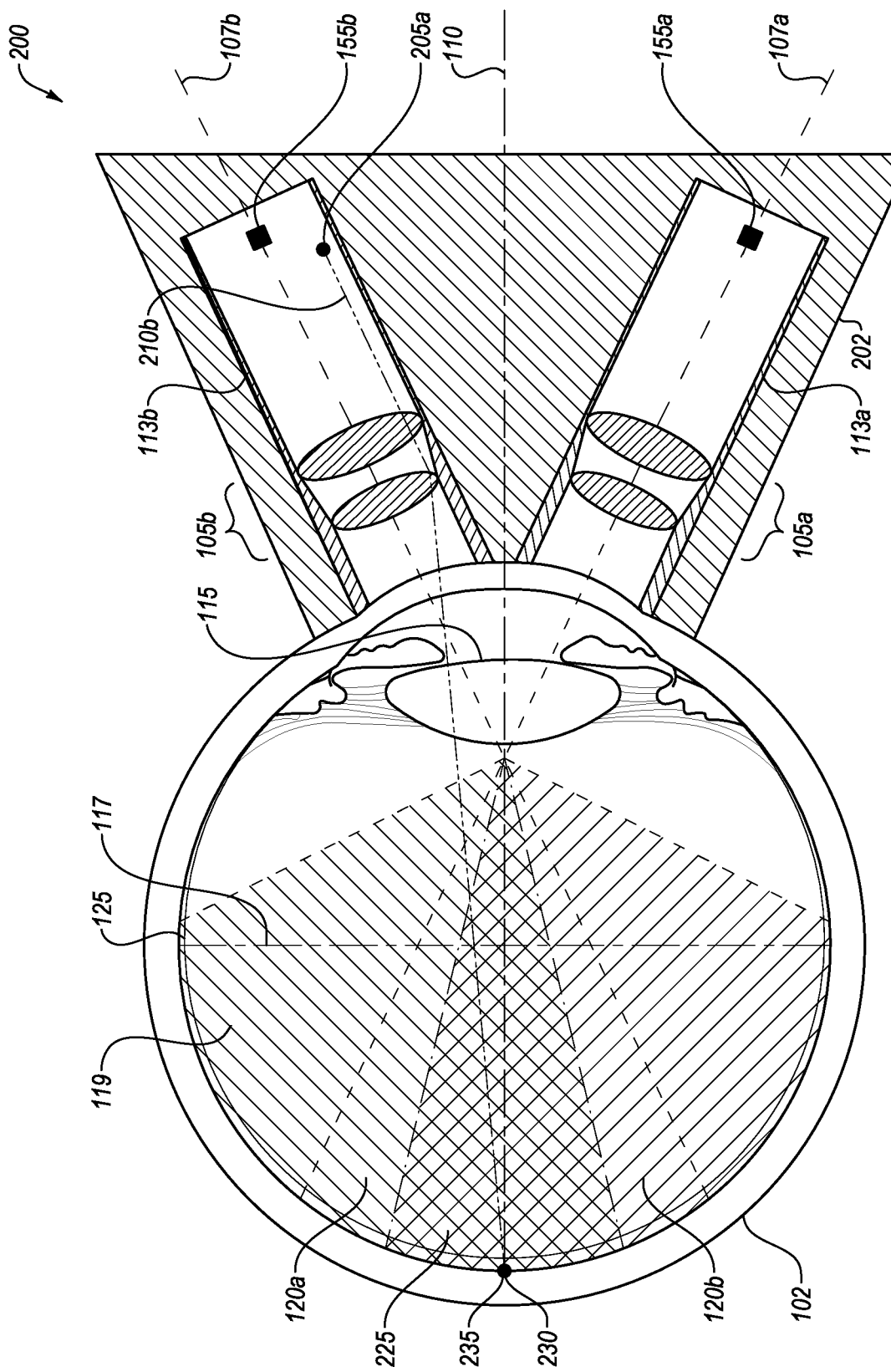
FIG. 2C illustrates yet another example embodiment of a cross-sectional side view of the optical imaging device of FIG. 2A using primary fixation for imaging the eye.

FIG. 2C illustrates yet another example embodiment of a cross-sectional side view of the optical imaging device 200 of FIG. 2A using primary fixation for imaging the eye 102, all arranged according to one or more embodiments of the present disclosure. As illustrated, the optical imaging device 200 may be the same as or similar to the optical imaging device 200 shown in FIG. 2A, with the addition of the optical lenses 105a, the optical imaging pathway 107a, the imaging channel 113a, and the image capturing device 155a of FIG. 1B. Further illustrated is an overlap region 225, a fovea 230 of the eye 102, and an artifact 235 of the primary fixation target 205a.

In some embodiments, the overlap region 225 may include a portion of the eye 102 that is covered by both the imaging region 120a and the imaging region 120b. In these or other embodiments, the overlap region 225 may be positioned to include the fovea 230 and/or the central axis 110 of the eye. Additionally or alternatively, the overlap region 225 may be positionally based on the optical imaging pathways 107a/107b.

In some embodiments, and as illustrated in FIG. 2C in the overlap region 225, the artifact 235 may be generated onto the retina 125, for example, at or near the fovea 230. In other embodiments, the artifact 235 may not be positioned at or near the fovea 230. In these or other embodiments, the artifact 235 may be positioned within the overlap region 225. With the artifact 235 positioned within the overlap region 225, the artifact 235 may be removed when stitching together images for composite image generation.

In some embodiments, the artifact 235 may be an optical effect of the primary fixation target 205. In a first example, the artifact 235 may include a display of optical signals intersecting the retina 125. For instance, the optical signals may be emitted by the primary fixation target 205a along the primary fixation target projection path 210a. When the optical signals intersect the retina 125, the artifact 235 may be generated. Thus, in some embodiments, the artifact 235 may include a colored dot, for example, such as a red or green dot depending on the color of optical signals emitted by the primary fixation target 205a. Additionally or alternatively, the shape and size of the artifact 235 may depend on the shape and size of the primary fixation target 205a emitting optical signals. In these or other embodiments, the artifact 235 resulting from optical signals emitted by the primary fixation target 205a may be turned on/off as desired, e.g., for image capturing by the image capturing device 155b.

In a second example, the artifact 235 may include a shadow displayed onto the retina 125. The artifact 235 in the form of the shadow may or may not be configured to be turned on/off as described above with optical signals. For instance, the primary fixation target 205a may be positioned between the eye 102 and an illumination source (e.g., for illuminating portions of the eye 102 to be imaged), such that the primary fixation target 205a casts a shadow onto the eye 102 when the illumination source emits illumination towards the eye that is at least partially blocked by the primary fixation target 205a. Additionally or alternatively, the artifact 235 may include a blurred, blackened, or obscured portion (e.g., a dot) in an image that corresponds to where the primary fixation target 205a is relatively positioned between the illumination source and the eye 102. For instance, in the blurred, blackened, or obscured portion example of the artifact 235, the artifact 235 may not be actually displayed or projected against the retina 125, but may instead be an optical effect detected only in image when positioning the primary fixation target 205a in the same imaging channel 113b as the illumination source (not shown). Thus, in some embodiments, the artifact 235 may result from shared optical lenses 105b and/or the shared imaging channel 113b between any of the optical imaging pathway 107a, the primary fixation target projection path 210a, and an optical illumination pathway (not shown), and/or from relative positioning of the primary fixation target 205a thereto.

Figure 2D:
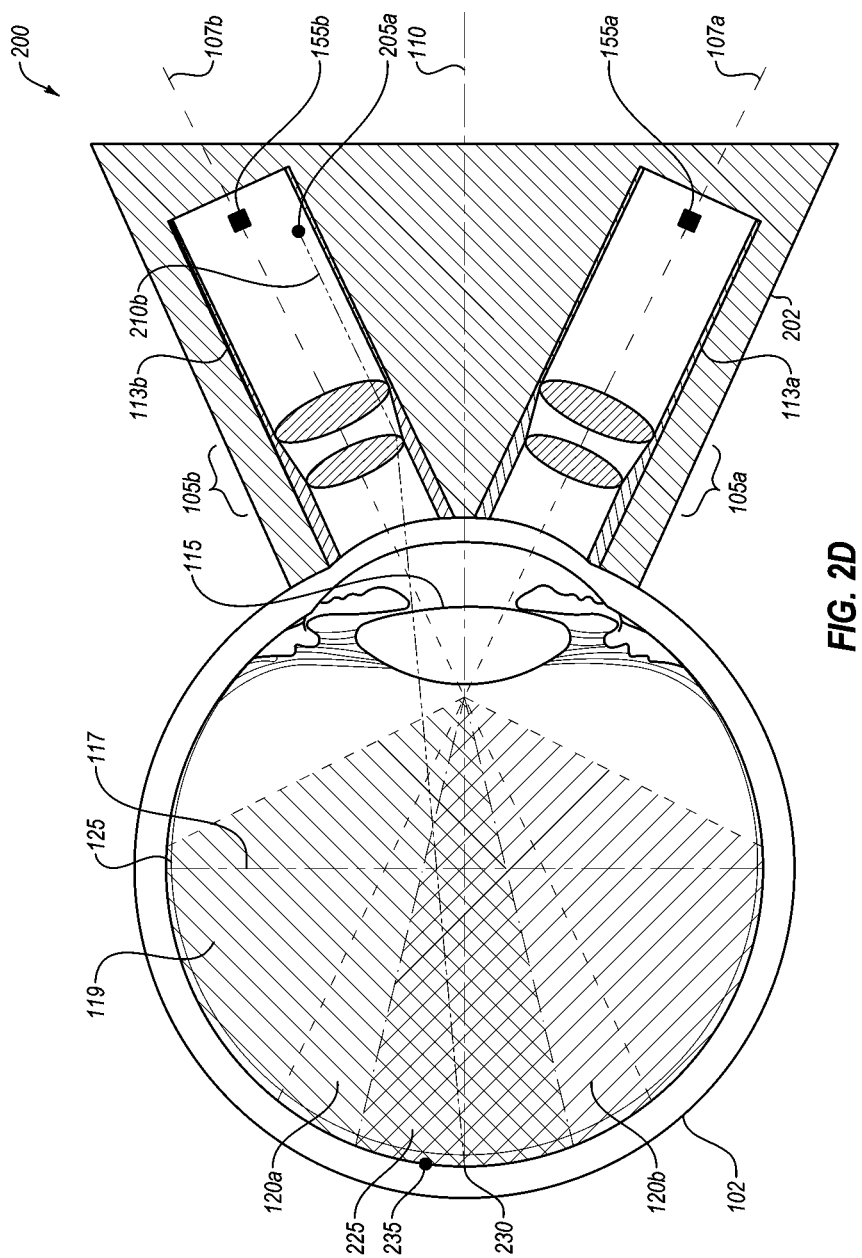
FIG. 2D illustrates yet an additional example embodiment of a cross-sectional side view of the optical imaging device of FIG. 2A using primary fixation for imaging the eye.

In some embodiments, the shadow cast by the primary fixation target 205 a may be positioned on the retina 125 where the primary fixation target projection path 210 a intersects the retina 125. Accordingly, in some embodiments, an optical illumination pathway of the illumination source may be collinear with the primary fixation target projection path 210 a such that the primary fixation target 205 a and the illumination source are aligned relative to each other. In other embodiments, such as illustrated in FIG. 2D, the shadow cast by the primary fixation target 205 a may be positioned on the retina 125 at a different retinal location than whether the primary fixation target projection path 210 a intersects the retina 125. For example, the optical illumination pathway of the illumination source may not be collinear with the primary fixation target projection path 210 a such that the primary fixation target 205 a and the illumination source are not aligned relative to each other.

In some embodiments, at least one of the other imaging channels 113, such as the imaging channel 113a, does not include a primary fixation target nor a projection of such a primary fixation target at the precise same location as the artifact 235 discussed above. In these or other embodiments, a seamless composite image from multiple imaging channels 113 may be achieved such that the artifact 235 is not visible in the composite image. Such a seamless composite image may be a result of software analytics configured to stitch together multiple overlapping images, for example, of the imaging regions 120a/120b. Additionally or alternatively, by combining the two or more overlapping portions that include the overlapping region 225 affected by the artifact 235, the artifact 235 may be ignored or removed when generating the composite image.

Modifications, additions, or omissions may be made to the embodiments of FIGS. 2A-2D without departing from the scope of the present disclosure. For example, in some embodiments, the channels 113 a/113 b may include any number of other components that may not be explicitly illustrated or described. Additionally or alternatively, for example, the primary fixation target 205 a may create the artifact 235 anywhere along the retina 125 than may be explicitly illustrated or described.

Figure 3:
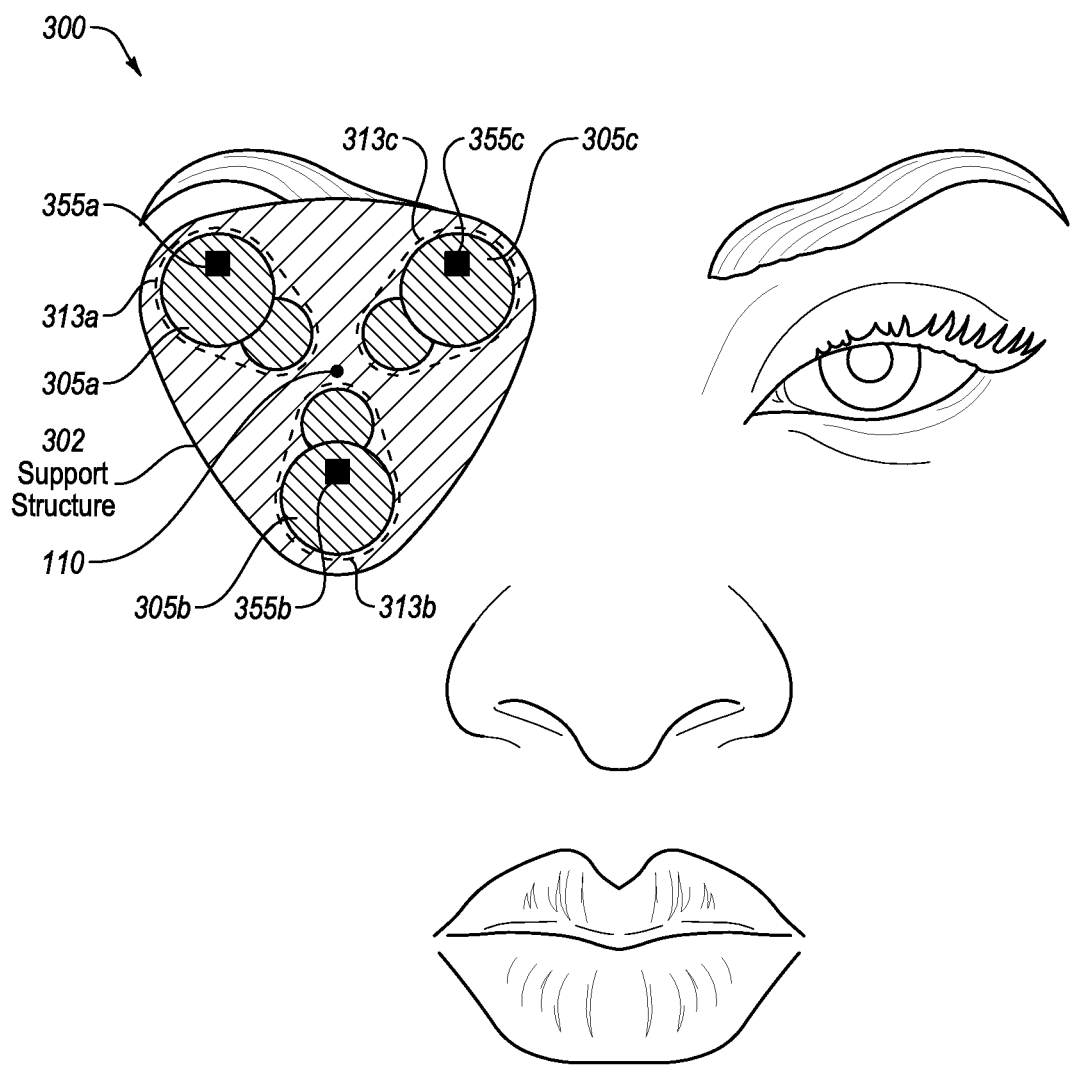
FIG. 3 illustrates a cross-sectional front view of an optical imaging device for imaging the eye in FIG. 1A, relative to facial features.

FIG. 3 illustrates a cross-sectional front view of an optical imaging device 300 for imaging the eye, relative to facial features, all arranged according to one or more embodiments of the present disclosure. As illustrated, the optical imaging device 300 includes a support structure 302, lenses 305a-305c, imaging channels 313a-313c, and image capturing devices 355a-355c. In some embodiments, the optical imaging device 300 may be aligned relative to a central axis 110 of an eye. Additionally or alternatively, the lenses 305a-305c, the imaging channels 313a-313c, and the image capturing devices 355a-355c may be the same as or similar to the lenses 105a-105b, the imaging channels 113a-113b, and the image capturing devices 155a-155b, respectively, of FIG. 1B.

The support structure 302 may be the same as or similar to the support structure described in U.S. patent application Ser. No. 16/217,750 entitled MULTIPLE OFF-AXIS CHANNEL OPTICAL IMAGING DEVICE UTILIZING UPSIDE-DOWN PYRAMIDAL CONFIGURATION filed on Dec. 12, 2018, the contents of which are hereby incorporated by reference in their entirety. In these or other embodiments, the support structure 302 may house the lenses 305a-305c, the imaging channels 313a-313c, and the image capturing devices 355a-355c. Additionally or alternatively, the support structure 302 may be sized and shaped for ergonomic purposes, e.g., to more suitably interface with facial features of a patient. In other embodiments, additional configurations of the support structure 302, other than an upside-down pyramidal configuration, may be implemented. For example, any suitable configuration permitting additional or increased clearance between the support structure 302 and one or both of a brow and a nose is contemplated herein. Additionally or alternatively, any suitable configuration permitting multiple imaging channels 313, e.g., two or more imaging channels 313, for imaging the eye may be implemented. For example, the support structure 302 may take a frustoconical shape.

In some embodiments, the optical imaging device 300 may be rotated by rotating the support structure 302. For example, by rotating the support structure 302 in a clockwise or counter-clockwise direction about the central axis 110 of the eye, different portions of the eye may be imaged.

In some embodiments, more or fewer numbers of lenses 305 may be used within any of the imaging channels 313, e.g., to permit more suitable imaging of a particular area of the eye. Additionally or alternatively, the lenses 305 may be sized and shaped to fill an inner diameter of the imaging channels 313 that house the lenses 305, while in other embodiments, the lenses 305 may be sized and shaped to be less than the inner diameter of the imaging channel 313. Additionally or alternatively, one or more components may be positioned between, adjacent to, distal to, and/or proximal to any of the lenses 305.

In some embodiments, the imaging channels 313a-313c may be angled relative to each other. Additionally or alternatively, the imaging channels 313a-313c may be angled relative to the central axis 110 of the eye such that no imaging channel 313 may be coaxial with the central axis 110 of the eye. In other embodiments, at least one imaging channel 313 may be coaxial with the central axis 110 of the eye. The imaging channels 313a-313c may be sized, shaped and/or positioned within the support structure 302 in any suitable configuration, e.g., depending on an imaging application or pupil size of the eye to be imaged. Additionally or alternatively, the imaging channels 313a-313c may be sized, shaped and/or positioned relative to the eye, e.g., the central axis 110 of the eye depending on an imaging application or pupil size of the eye to be imaged.

Additionally or alternatively, more or fewer imaging channels 313 may be utilized in the optical imaging device 300, e.g., to facilitate up to three hundred and sixty degrees around the eye of image acquisition capability. For example, the optical imaging device 300 may include imaging channels 313 numbering between two and twelve imaging channels 313, such as between two and three, three and four, four and five, five and six, six and seven, seven and eight, eight and nine, or nine and ten. In some embodiments, more imaging channels 313 may be utilized to provide a more circumferential view of the eye while less imaging channels 313 may provide less of a circumferential view of the eye, given that each imaging channel 313 may only capture a portion of the eye. In these or other embodiments, the image capturing devices 355 may capture images all at the same time or in rapid succession, for example, using a rapid multi-plex. In this manner, for example, topographical information or a topographical profile may be generated at representative locations, e.g., at 12 o'clock, 2 o'clock, 4 o'clock, 6 o'clock, 8 o'clock, and 10 o'clock positions of the eye. Additionally or alternatively, one or more of the imaging channels 313 may be rotated relative to the support structure 302. For example, while the support structure 302 remains in a static position relative to the eye and/or facial features of the patient, any of the imaging channels 313 may be rotated inside the support structure 302. Such internal rotation of the imaging channels 313 may enable different portions and/or perspectives of the eye to be imaged.

Modifications, additions, or omissions may be made to the embodiments of FIG. 3 without departing from the scope of the present disclosure. For example, in some embodiments, the support structure 302 may include any number of other components that may not be explicitly illustrated or described. Additionally or alternatively, the support structure 302 may be sized, shaped, and/or oriented relative to facial features in other suitable ways than may be explicitly illustrated or described. Additionally or alternatively, for example, the imaging channels 313a-313c may be sized, shaped, positioned, and/or oriented within the support structure 302 in other suitable ways than may be explicitly illustrated or described.

Figure 4:
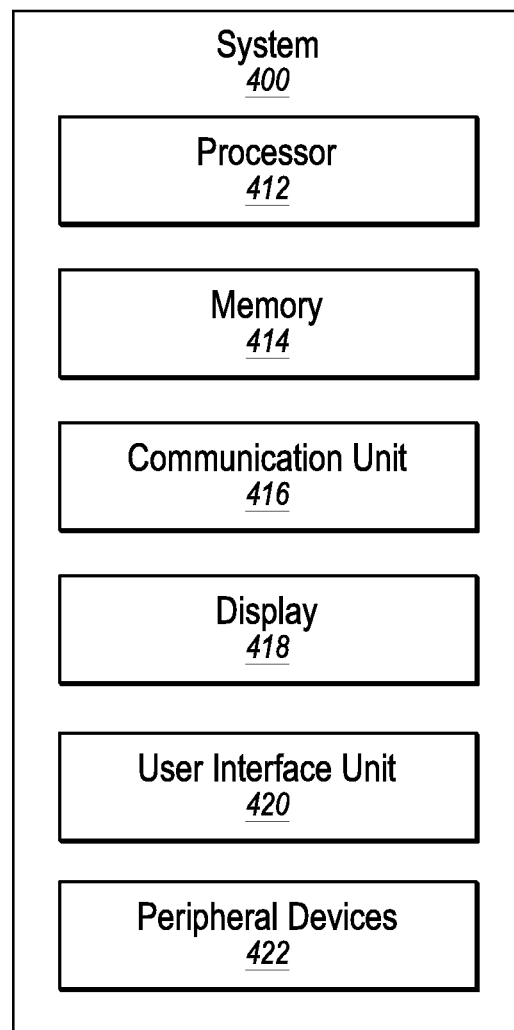
FIG. 4 illustrates an example system that may be used in multiple off-axis channel imaging of the eye.

FIG. 4 illustrates an example system 400 that may be used in multiple off-axis channel imaging of the eye. The system 400 may be arranged in accordance with at least one embodiment described in the present disclosure. The system 400 may include a processor 410, memory 412, a communication unit 416, a display 418, a user interface unit 420, and a peripheral device 422, which all may be communicatively coupled. In some embodiments, the system 400 may be part of any of the systems or devices described in this disclosure.

Generally, the processor 410 may include any suitable special-purpose or general-purpose computer, computing entity, or processing device including various computer hardware or software modules and may be configured to execute instructions stored on any applicable computer-readable storage media. For example, the processor 410 may include a microprocessor, a microcontroller, a digital signal processor (DSP), an application-specific integrated circuit (ASIC), a Field-Programmable Gate Array (FPGA), or any other digital or analog circuitry configured to interpret and/or to execute program instructions and/or to process data.

Although illustrated as a single processor in FIG. 4, it is understood that the processor 410 may include any number of processors distributed across any number of networks or physical locations that are configured to perform individually or collectively any number of operations described in this disclosure. In some embodiments, the processor 410 may interpret and/or execute program instructions and/or process data stored in the memory 412. In some embodiments, the processor 410 may execute the program instructions stored in the memory 412.

For example, in some embodiments, the processor 410 may execute program instructions stored in the memory 412 that are related to determining whether generated sensory data indicates an event and/or determining whether the event is sufficient to determine that the user is viewing a display of a device such that the system 400 may perform or direct the performance of the operations associated therewith as directed by the instructions. In these and other embodiments, instructions may be used to perform one or more operations or functions described in the present disclosure.

The memory 412 may include computer-readable storage media or one or more computer-readable storage mediums for carrying or having computer-executable instructions or data structures stored thereon. Such computer-readable storage media may be any available media that may be accessed by a general-purpose or special-purpose computer, such as the processor 410. By way of example, and not limitation, such computer-readable storage media may include non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store particular program code in the form of computer-executable instructions or data structures and which may be accessed by a general-purpose or special-purpose computer. Combinations of the above may also be included within the scope of computer-readable storage media. Computer-executable instructions may include, for example, instructions and data configured to cause the processor 410 to perform a certain operation or group of operations as described in this disclosure. In these and other embodiments, the term "non-transitory" as explained in the present disclosure should be construed to exclude only those types of transitory media that were found to fall outside the scope of patentable subject matter in the Federal Circuit decision of *In re Nuijten,* 500 F.3d 1346 (Fed. Cir. 2007). Combinations of the above may also be included within the scope of computer-readable media.

The communication unit 416 may include any component, device, system, or combination thereof that is configured to transmit or receive information over a network. In some embodiments, the communication unit 416 may communicate with other devices at other locations, the same location, or even other components within the same system. For example, the communication unit 416 may include a modem, a network card (wireless or wired), an infrared communication device, a wireless communication device (such as an antenna), and/or chipset (such as a Bluetooth device, an 802.6 device (e.g., Metropolitan Area Network (MAN)), a Wi-Fi device, a WiMax device, cellular communication facilities, etc.), and/or the like. The communication unit 416 may permit data to be exchanged with a network and/or any other devices or systems described in the present disclosure.

The display 418 may be configured as one or more displays, like an LCD, LED, or other type of display. For example, the display 418 may be configured to present measurements, indicate warning notices, show tolerance ranges, display whether good/bad eye tissues are determined, and other data as directed by the processor 410.

The user interface unit 420 may include any device to allow a user to interface with the system 400. For example, the user interface unit 420 may include a mouse, a track pad, a keyboard, buttons, and/or a touchscreen, among other devices. The user interface unit 420 may receive input from a user and provide the input to the processor 410. In some embodiments, the user interface unit 420 and the display 418 may be combined.

The peripheral devices 422 may include one or more devices. For example, the peripheral devices may include a sensor, a microphone, and/or a speaker, among other peripheral devices. As examples, the sensor may be configured to sense changes in light, sound, motion, rotation, position, orientation, magnetization, acceleration, tilt, vibration, etc., e.g., as relating to an eye of a patient. Additionally or alternatively, the sensor may be part of or communicatively coupled to the optical imaging device as described in the present disclosure.

Modifications, additions, or omissions may be made to the system 400 without departing from the scope of the present disclosure. For example, in some embodiments, the system 400 may include any number of other components that may not be explicitly illustrated or described. Further, depending on certain implementations, the system 400 may not include one or more of the components illustrated and described.

In accordance with common practice, the various features illustrated in the drawings may not be drawn to scale. The illustrations presented in the present disclosure are not meant to be actual views of any particular apparatus (e.g., device, system, etc.) or method, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner. Additionally, the term "about" or "approximately" should be interpreted to mean a value within 10% of actual value.

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

Additionally, the use of the terms "first," "second," "third," etc., are not necessarily used herein to connote a specific order or number of elements. Generally, the terms "first," "second," "third," etc., are used to distinguish between different elements as generic identifiers. Absence a showing that the terms "first," "second," "third," etc., connote a specific order, these terms should not be understood to connote a specific order. Furthermore, absence a showing that the terms "first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

What is claimed is:

1. An optical imaging device, comprising:
a support structure; and
a plurality of imaging channels, each imaging channel of the plurality of imaging channels including a discrete optical imaging pathway, the plurality of imaging channels disposed within the support structure, the plurality of imaging channels aimed at different angles relative to each other such that each optical imaging pathway is directed towards a pupil of an eye; and
a primary fixation target positioned inside a first imaging channel of the plurality of imaging channels between optical illumination of the first imaging channel and the eye, the primary fixation target configured to emit optical signals along a primary fixation target projection path towards the pupil of the eye,
wherein an artifact of the primary fixation target is generated onto a portion of the eye to be imaged, the artifact in a form of a shadow cast by the primary fixation target blocking at least a portion of the optical illumination of the first imaging channel;
wherein the artifact of the primary fixation target is positioned at a first location of a retina; and
wherein the primary fixation target projection path intersects the retina at a second location different from the first location.

2. The optical imaging device of claim 1, wherein the primary fixation target projection path and an optical imaging pathway of at least one imaging channel of the plurality of imaging channels share one or more common optical lenses.

3. The optical imaging device of claim 1, wherein the primary fixation target projection path impinges on a prism.

4. The optical imaging device of claim 1, further comprising:
a plurality of image capturing devices, each image capturing device of the plurality of image capturing devices respectively associated with one of the plurality of imaging channels to capture digital photograph images of respective portions of the eye.

5. The optical imaging device of claim 4, wherein:
the digital photograph images from the plurality of imaging channels overlap each other at least in an overlap region and are stored in a storage device of the optical imaging device for stitching together such that the digital photograph images form a composite image; and
the artifact is positioned in the overlap region such that the artifact is omitted in the composite image.

6. The optical imaging device of claim 1, further comprising:
a plurality of sets of optical lenses, at least one lens in each of the sets of optical lenses having a fixed position within a respective imaging channel of the plurality of imaging channels.

7. A system comprising:
one or more processors configured to receive optical imaging data; and
an optical imaging device configured to generate optical imaging data, the optical imaging device communicatively coupled to the one or more processors, and the optical imaging device comprising:
a support structure; and
a plurality of imaging channels, each imaging channel of the plurality of imaging channels including a discrete optical imaging pathway, the plurality of imaging channels disposed within the support structure, the plurality of imaging channels aimed at different angles relative to each other such that each optical imaging pathway is directed towards a pupil of an eye; and
a primary fixation target positioned inside a first imaging channel of the plurality of imaging channels between optical illumination of the first imaging channel and the eye, the primary fixation target configured to emit optical signals along a primary fixation target projection path towards the pupil of the eye,
wherein an artifact of the primary fixation target is generated onto a portion of the eye to be imaged, the artifact in a form of a shadow cast by the primary fixation target blocking at least a portion of the optical illumination of the first imaging channel;
wherein the artifact of the primary fixation target is positioned at a first location of a retina; and
wherein the primary fixation target projection path intersects the retina at a second location different from the first location.

8. The system of claim 7, wherein the primary fixation target projection path and an optical imaging pathway of at least one imaging channel of the plurality of imaging channels share one or more common optical lenses.

9. The system of claim 7, wherein the primary fixation target projection path impinges on a prism.

10. The system of claim 7, further comprising:
a plurality of image capturing devices, each image capturing device of the plurality of image capturing devices respectively associated with one of the plurality of imaging channels to capture digital photograph images of respective portions of the eye.

11. The system of claim 10, wherein:
the digital photograph images from the plurality of imaging channels overlap each other at least in an overlap region and are stored in a storage device of the optical imaging device for stitching together such that the digital photograph images form a composite image; and
the artifact is positioned in the overlap region such that the artifact is omitted in the composite image.

12. The system of claim 7, further comprising:
a plurality of sets of optical lenses, at least one lens in each of the sets of optical lenses having a fixed position within a respective imaging channel of the plurality of imaging channels.

* * * * *